US012746513B2

(12) United States Patent
Cates et al.

(10) Patent No.: US 12,746,513 B2
(45) Date of Patent: Sep. 29, 2026

(54) VESSEL, SYSTEM, AND ASSOCIATED METHOD FOR PRODUCT CONCENTRATION

(71) Applicant: Repligen Corporation, Waltham, MA (US)

(72) Inventors: Steven V. Cates, Lakewood, CA (US); Rudolf Pavlik, Huntington Beach, CA (US); Bao Le, Redondo Beach, CA (US)

(73) Assignee: Repligen Corporation, Waltham, MA (US)

(*) Notice: Subject to any disclaimer, the term of this patent is extended or adjusted under 35 U.S.C. 154(b) by 900 days.

(21) Appl. No.: 18/071,899

(22) Filed: Nov. 30, 2022

(65) Prior Publication Data

US 2023/0211292 A1 Jul. 6, 2023

Related U.S. Application Data

(60) Provisional application No. 63/295,154, filed on Dec. 30, 2021.

(51) Int. Cl.
*B01D 61/18* (2006.01)
*B01D 61/14* (2006.01)
(Continued)

(52) U.S. Cl.
CPC ........... *B01D 61/18* (2013.01); *B01D 61/145* (2013.01); *B01F 27/851* (2022.01); *C12M 47/02* (2013.01);
(Continued)

(58) Field of Classification Search
CPC ...... B01D 61/18; B01D 61/145; B01D 63/02; B01D 63/082; B01D 2311/25;
(Continued)

(56) References Cited

U.S. PATENT DOCUMENTS 4,256,839 A * 3/1981 Solomons .............. C12M 27/02 435/295.1
2009/0130704 A1* 5/2009 Gyure .................... C12M 39/00 435/292.1
(Continued)

FOREIGN PATENT DOCUMENTS

CN 109576139 A 4/2019
CN 113186090 A 7/2021
(Continued)

OTHER PUBLICATIONS

International Search Report and Written Opinion for Application No. PCT/US2022/051333 dated May 31, 2023.

*Primary Examiner* — Pranav N Patel
(74) *Attorney, Agent, or Firm* — KDW Firm PLLC

(57) ABSTRACT

Vessel configured to facilitate concentration of a product in a solution. The vessel may include outlet ports to deliver the solution to a processing system (such as a filtration system), and inlet ports. The inlet ports may be at progressively lower levels for return of fluid thereto reduced in volume as a result of filtration thereof. A smaller volume sump may be provided below a main tank of the vessel to facilitate concentration of the solution. The sump may include ridges facilitating collection of the product of interest from the solution, and/or reinforcing the sump walls, and optionally forming a vortex breaker. A spray ball may be provided to spray materials, such as buffer solution, into the vessel. The spray ball may direct materials to facilitate retrieval of product from the vessel. One or more components of the vessel may be advantageously formed of disposable material for single use thereof.

20 Claims, 5 Drawing Sheets

(51) Int. Cl.
*B01F 27/85* (2022.01)
*C12M 1/00* (2006.01)
*B01D 63/02* (2006.01)
*B01D 63/08* (2006.01)

(52) U.S. Cl.
CPC ............ *B01D 63/02* (2013.01); *B01D 63/082* (2013.01); *B01D 2311/25* (2013.01); *B01D 2315/10* (2013.01)

(58) Field of Classification Search
CPC .. B01D 2315/10; B01F 27/851; C12M 47/02; C12M 47/12; C12M 29/18; C12M 33/14; C12M 23/28; C12M 27/06
See application file for complete search history.

(56) References Cited

U.S. PATENT DOCUMENTS

| | | | | |
|---|---|---|---|---|
| 2013/0005014 | A1* | 1/2013 | Bell | C12M 27/02<br>435/168 |
| 2017/0349874 | A1* | 12/2017 | Jaques | B01F 27/191 |
| 2017/0369828 | A1* | 12/2017 | Mietzner | C12M 23/14 |
| 2019/0322975 | A1* | 10/2019 | Nakai | C12M 29/04 |
| 2020/0165558 | A1* | 5/2020 | Shevitz | C12M 27/04 |
| 2022/0364126 | A1* | 11/2022 | Alibek | C12M 29/20 |

FOREIGN PATENT DOCUMENTS

| | | | |
|---|---|---|---|
| EA | 032296 | B1 | 5/2019 |
| EP | 1386575 | A1 | 2/2004 |

* cited by examiner

VESSEL, SYSTEM, AND ASSOCIATED METHOD FOR PRODUCT CONCENTRATION

CROSS-REFERENCE TO RELATED APPLICATIONS

The present application claims the benefit of priority under 35 U.S.C. § 119 to U.S. Provisional Application Ser. No. 63/295,154, titled "VESSEL, SYSTEM, AND ASSOCIATED METHOD FOR PRODUCT CONCENTRATION" and filed Dec. 30, 2021, the entirety of which application is incorporated by reference herein for all purposes.

FIELD

The present disclosure relates generally to the field of vessels for containing fluid solutions, such as in biological, pharmaceutical, biopharmaceutical, biotechnological, bioprocess, food, or beverage industries. More particularly, the present disclosure relates to vessels which may be used in fluid filtration systems, and associated systems and methods for concentrating a target product in the feedstream therein for retrieval therefrom.

BACKGROUND

Concentration of one or more products in a fluid solution may be desirable or necessary for any of a number of reasons. For instance, certain products are initially formed or processed in a fluid solution at a low, dilute concentration. However, downstream processing of such products may be optimized or more desirable at a higher concentration of the product.

More particularly, sample preparation of macromolecule solutions, such as proteins, enzymes, antibodies, and viruses, often yield large volumes of diluted macrosolutes in buffers that are incompatible with downstream processes or detection. Virus isolation and propagation methods, in particular, are critical in research, vaccine production, and diagnostic workflows. Virus stocks are used to study viral biology and pathogenesis. Vaccine production requires small-scale and large-scale preparation of virus. Isolation and concentration of virus and products thereof in cell culture remains a useful approach when viable isolates are needed, when viable and nonviable virus must be differentiated, and/or where culture-based methods are able to provide results faster than non-culture methods.

Virus stocks may be generated by propagating viruses in a cell culture. For instance, cultured cells may be inoculated with viral stock from seed virus, a commercial source, or infected tissue. After incubation, the infected cells are lysed to harvest viral particles, or released virus is harvested directly from cell supernatants.

In order to achieve high titer virus stocks, it is necessary to concentrate purified virus particles. Various methods of concentrating the virus include ultrafiltration. The correct choice of device, membrane material, molecular weight limit or cut-off, filtration speed, filtration time, and buffer composition are critical for high recovery of infective viral particles.

Diafiltration is a variation of ultrafiltration, designed to increase the concentration of high molecular weight components (macro-solute) and to decrease the concentration of low molecular weight components (micro-solute). Diafiltration includes adding fresh solvent to the feed solution to replenish the volume of the feed solution being ultrafiltered, and/or to wash away small molecules (such as salts) from the retained macromolecules which are the target product of interest to be collected from the process. Buffer solutions may be added during the process to modify the properties of the solution in which the target product (e.g., virus) is contained. This rebuffering step should stabilize the product (e.g., virus) and ensure the correct conditions (e.g., physiological conditions) for the desired (e.g., clinical) applications, or otherwise modify the composition of the solution for the final concentrated product to be retrieved from the system.

Various ultrafiltration and diafiltration devices, systems, and processes are known. However, new intensification processes require very high concentration of biologics by large orders of magnitude (e.g., initial concentration of 2.5 mg/ml to final concentration of 250 mg/ml).

SUMMARY

This summary of the disclosure is given to aid understanding, and one of skill in the art will understand that each of the various aspects and features of the disclosure may advantageously be used separately in some instances, or in combination with other aspects and features of the disclosure in other instances. No limitation as to the scope of the claimed subject matter is intended by either the inclusion or non-inclusion of elements, components, or the like in this summary.

In accordance with various principles of the present disclosure, a fluid vessel has a vessel tank with at least one inlet port defined in a sidewall thereof, and a sump assembly fluidly coupled below the vessel tank and having at least one inlet port defined in a side wall thereof, the sump assembly having a sump vessel with an internal volume for holding fluid smaller than the internal volume of the vessel tank.

In some embodiments, a first inlet port and a second inlet port are defined in a sidewall of the vessel tank, the second inlet port being lower than the first inlet port to deliver feedstream into the vessel tank at a lower height than delivered through the first inlet port.

In some embodiments, the vessel tank is formed of a disposable polymeric material.

In some embodiments, the sump vessel is formed of a disposable material.

In some embodiments, at least one ridge extends inwardly from a sidewall of the sump vessel. In some embodiments, the ridge forms a vortex breaker.

In some embodiments, the vessel tank is configured to contain at least 100 liters of fluid, and the sump vessel is configured to contain no more than about 10 liters of fluid.

In some embodiments, the fluid vessel includes a first impeller configured to stir fluid within the vessel tank, and a separately controllable second impeller configured to stir fluid in the sump vessel.

In some embodiments, the fluid vessel includes a spray ball extending from a top of the fluid vessel into the vessel tank and formed of a disposable material. The spray ball is configured to spray buffer solution into the vessel tank directed to the interior of the sidewall of the vessel tank.

In some aspects, a fluid vessel is disclosed as a single-use fluid vessel having a vessel tank formed of a disposable material; and a spray ball, formed of a disposable material, and extending from a top of the fluid vessel into the vessel tank.

In some embodiments, the spray ball is formed of an irradiatable sterilizable material.

In some embodiments, the spray ball includes a hollow stem having a plurality of perforations therethrough configured to direct material through the hollow stem towards the interior of the sidewall of the vessel tank.

In some embodiments, the spray ball is configured to spray buffer solution into the vessel tank directed to the interior of the sidewall of the vessel tank to return materials stuck on the interior of the sidewall of the vessel tank to fluid contained within the vessel tank.

In some embodiments, the vessel tank is formed of a flexible polymeric material.

In accordance with various principles of the present disclosure, a system for processing a fluid solution includes a fluid vessel, a processing system, and a fluid line assembly fluidly coupling components of the fluid vessel with the processing system. The fluid vessel include a vessel tank having a first volume, and a sump assembly having a second volume smaller than the first volume and fluidly coupled to a bottom of the vessel tank. The fluid line assembly fluidly couples the vessel tank and the sump assembly with the processing system. In some embodiments, the fluid line assembly includes a vessel outlet feed line fluidly coupling the fluid vessel with the processing system; a first return line fluidly coupled with a sidewall of the vessel tank at a first height along the fluid vessel to return fluid processed in the processing system to the vessel tank; a second return line fluidly coupled with a sidewall of the vessel tank at a second height along the fluid vessel lower than the first height to return fluid processed in the processing system to the vessel tank; and a sump return line fluidly coupled with the sump assembly below the first return line and the second return line.

In some embodiments, the processing system includes a filter unit.

In some embodiments, the system further may include a spray ball configured to spray material through the top of the vessel tank and towards the interior of the vessel tank sidewall. In some embodiments, the spray ball is coupled to a feed line for buffer solution and is configured to spray buffer solution towards the interior of the vessel tank sidewall. In some embodiments, the spray ball is formed of a disposable irradiatable material.

In some embodiments, at least one of the vessel tank and at least a portion of the sump vessel is formed of a disposable material.

These and other features and advantages of the present disclosure, will be readily apparent from the following detailed description, the scope of the claimed invention being set out in the appended claims. While the following disclosure is presented in terms of aspects or embodiments, it should be appreciated that individual aspects can be claimed separately or in combination with aspects and features of that embodiment or any other embodiment.

BRIEF DESCRIPTION OF THE DRAWINGS

Non-limiting embodiments of the present disclosure are described by way of example with reference to the accompanying drawings, which are schematic and not intended to be drawn to scale. The accompanying drawings are provided for purposes of illustration only, and the dimensions, positions, order, and relative sizes reflected in the figures in the drawings may vary. For example, devices may be enlarged so that detail is discernable, but is intended to be scaled down in relation to, e.g., fit within a working channel of a delivery catheter or endoscope. In the figures, identical or nearly identical or equivalent elements are typically represented by the same reference characters, and similar elements are typically designated with similar reference numbers differing in increments of 100, with redundant description omitted. For purposes of clarity and simplicity, not every element is labeled in every figure, nor is every element of each embodiment shown where illustration is not necessary to allow those of ordinary skill in the art to understand the disclosure.

The detailed description will be better understood in conjunction with the accompanying drawings, wherein like reference characters represent like elements, as follows.

DETAILED DESCRIPTION

Figure 1:
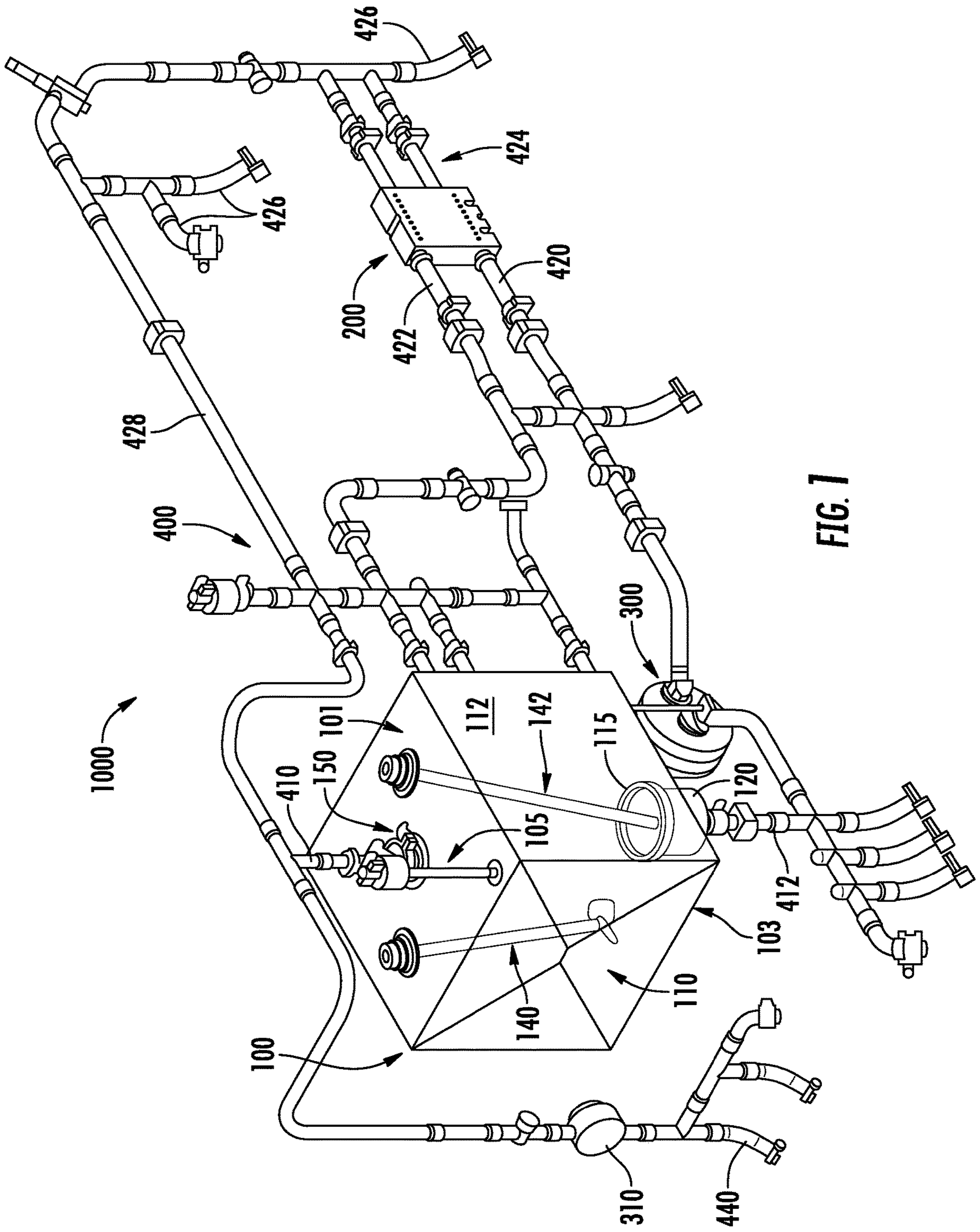
FIG. 1 illustrates a perspective view of a filtration system formed in accordance with aspects of the present disclosure.

The following detailed description should be read with reference to the drawings, which depict illustrative embodiments. It is to be understood that the disclosure is not limited to the particular embodiments described, as such may vary. All apparatuses and systems and methods discussed herein are examples of apparatuses and/or systems and/or methods implemented in accordance with one or more principles of this disclosure. Each example of an embodiment is provided by way of explanation and is not the only way to implement these principles but are merely examples. Thus, references to elements or structures or features in the drawings must be appreciated as references to examples of embodiments of the disclosure, and should not be understood as limiting the disclosure to the specific elements, structures, or features illustrated. Other examples of manners of implementing the disclosed principles will occur to a person of ordinary skill in the art upon reading this disclosure. In fact, it will be apparent to those skilled in the art that various modifications and variations can be made in the present disclosure without departing from the scope or spirit of the present subject matter. For instance, features illustrated or described as part of one embodiment can be used with another embodiment to yield a still further embodiment. Thus, it is intended that the present subject matter covers such modifications and variations as come within the scope of the appended claims and their equivalents.

It will be appreciated that the present disclosure is set forth in various levels of detail in this application. In certain instances, details that are not necessary for one of ordinary skill in the art to understand the disclosure, or that render other details difficult to perceive may have been omitted. The terminology used herein is for the purpose of describing particular embodiments only, and is not intended to be limiting beyond the scope of the appended claims. Unless defined otherwise, technical terms used herein are to be understood as commonly understood by one of ordinary skill in the art to which the disclosure belongs. All of the devices and/or methods disclosed and claimed herein can be made and executed without undue experimentation in light of the present disclosure.

In accordance with various principles of the present disclosure, a vessel is configured to contain a fluid solution, as well as to allow the fluid solution to be drawn from the vessel and returned to the vessel. It will be appreciated that the vessel may alternately be referenced herein as a bioprocess containment vessel, a containment vessel, a bioreactor vessel, a retentate vessel, a stirred-tank bioreactor, a bioreactor container, a mixer bag, a bag, a container, or the like, without intent to limit. Furthermore, it will be appreciated that the fluid solution may alternately be referenced herein as a simply a fluid or simply a solution, or a feed, a feed solution, a feedstream, a feedstream solution, a medium, a fluid medium, etc., without intent to limit. The vessel may be a part of a fluid system in which the fluid solution therein is processed.

In some embodiments, the vessel is configured to allow fluid solution to be returned thereto at more than one level or height. In some embodiments, the vessel is configured to facilitate concentration of a component or product (such terms being used interchangeably herein without intent to limit) within the fluid solution, with a method which optionally uses additional components of the fluid system. The vessel may be sized, shaped, configured, and/or dimensioned to have a reduced volume section which may facilitate concentration of a component of the fluid solution contained within the vessel. In some embodiments, various components of the system may be particularly configured for single use, such as formed of materials considered, in the industry thereof, to be disposable. For instance, the vessel may be configured for single use and formed of a material considered by those of ordinary skill in the art to be disposable. Specifically, a single-use vessel is formed of a material which is generally not reused. The material may be sterilizable for use of the vessel in sterile fluid processes.

Advantageously, impellers may be used to agitate a fluid solution being concentrated, such as to create a desired hydrodynamic environment for the target product, to maintain homogeneity of the solution, to reduce the opportunity for product to settle, etc. In embodiments in which an impeller (which may be alternately referenced herein as an agitator or stirrer without intent to limit) is used to stir the fluid solution, a separate impeller may be provided for the reduced volume section of the vessel.

The fluid solution to be contained and/or processed within the vessel may be any of a variety of fluid solutions in the biological, pharmaceutical, biopharmaceutical, biotechnological, bioprocess, food, or beverage industry. The fluid system may be a feed-retentate filtration loop for concentrating a component or product of interest in a fluid solution. The product of interest may then be retrieved in a form which is better suited for further use or processing. It will be appreciated that terms such as component or product may be used interchangeably herein without intent to limit. The product may be considered a "product of interest" in the sense that such product is intended to be collected for further processing or otherwise. It will be appreciated that the product of interest may alternately be referenced herein, without intent to limit, as a target product. The fluid solution may be the retentate of an upstream filtration process (e.g., harvested product of a bioreactor in a fluid medium). In some embodiments, the fluid solution is a clarified solution or supernatant resulting from centrifugation or filtration of a cell culture. The product may be concentrated by a system and/or within a vessel formed in accordance with various principles of the present disclosure, such as with a process in accordance with various principles of the present disclosure. In some embodiments, the product is one or more proteins produced or expressed by host cells in an upstream process. In some embodiments, the product includes cells, such as the host cells and/or cell culture media. It will be appreciated that biologically derived proteins and antibodies used in the production of clinical as well as commercial materials may be concentrated with a system or vessel formed in accordance with various principles of the present disclosure. Various other fluid solutions with components to be concentrated may be processed using a vessel and/or system formed in accordance with various principles of the present disclosure, the present disclosure not being limited by a particular fluid solution and/or associated component.

A vessel formed in accordance with various principles of the present disclosure may be used in a fluid filtration system. If used in such manner, the vessel may be considered a recirculation process vessel or a retentate vessel of a filtration system. In some embodiments, the filtration system uses a tangential flow filtration ("TFF") system, such as with a cassette-type filter or hollow fiber filters. Fluid solution from the vessel is withdrawn (e.g., pumped) from the vessel and fed into the TFF system. The TFF system may remove some fluid medium to reduce the overall volume of the fluid solution (and thereby to increase the concentration of the product to be collected from the vessel and/or system). In some embodiments, the TFF system may use ultrafilters or microfilters to remove additional undesired materials from the fluid solution, such as waste products. The selection of the molecular weight cut-off of the TFF filter generally is determined by experimentation, and generally will affect how much of the lower molecular weight material is removed. It will be appreciated that the present disclosure should not be limited to use of a particular filtration system.

In some embodiments, the fluid system is an ultrafiltration/diafiltration ("UF/DF") system. A buffer exchange process may be performed within the vessel. A method of using a vessel and system formed in accordance with various principles of the present disclosure thus includes concentrating the final product of interest, as well as processing multiple volume diafiltration buffer exchange procedures. The buffer exchanges may utilize physiological buffer solutions selected based on the product of interest to be concentrated and recovered from the system. The buffer solutions may be added to the vessel with the use of a peristaltic buffer pump, or other suitable delivery device.

In accordance with various principles of the present disclosure, in some embodiments, diafiltration buffer solution is delivered into the vessel via a spray ball. The spray ball may be configured to spray the buffer along the side walls of the vessel. In embodiments in which the product to be concentrated are proteins, use of a spray ball in accordance with various principles of the present disclosure to spray buffer solution along the walls of the vessel wash the interior of the vessel as well as put the protein back into the solution rather than allowing the protein to aggregate on the walls of the vessel. It will be appreciated that spray balls similar to those described herein may be used to wash the walls of vessels used in processes such as those described herein (e.g., with a caustic solution prior to the process to be performed therein), such spray ball and vessels typically being formed of stainless steel or another material not considered to be single-use/disposable. In accordance with various principles of the present disclosure, a spray ball may be used for buffer exchange in a manner not previously typical of spray ball use. In accordance with various principles of the present disclosure, the vessel and/or the spray ball are formed from disposable materials, such as to be single-use components.

In some aspects of the present disclosure, various components of the system, such as the vessel, are intended to be single-use/disposable components. For instance, such components are designed for single use and formed from materials considered by those of ordinary skill in the art to be disposable which are generally not sterilized and reused (e.g., polymeric bags in contrast with stainless steel vats). In accordance with various principles of the present disclosure, a disposable process vessel includes a disposable process bag (e.g., a bioprocess containment vessel), such as formed of rigid, semi-rigid, or flexible polypropylene, polyethylene, polysulfone, etc. In some embodiments, the disposable process bag is formed of multiple polymeric layers such as dual inner layers of ultra-low-density polyethylene (ULDPE), an ethylene vinyl alcohol polymer (EVOH) gas barrier layer, and an outer layer of polyethylene (PE).

In some embodiments, the disposable process bag is formed in a generally cubical shape, with an opening in the bottom to fluidly communicate with an additional, smaller chamber. In some embodiments, the smaller chamber is a detachable lower sump assembly (or simply "sump" for the sake of simplicity and without intent to limit). The sump may include a top entry port in fluid communication with a bottom port in a disposable process bag, and a bottom outlet port for transfer of fluid within the vessel (disposable process bag and sump) for further processing (e.g., filtration) or for collection (e.g., of concentrated product). The bottom outlet port allows the vessel to achieve minimum recirculation volume as well as maximum drainability of the vessel. In some embodiments, the sump further includes a retentate side-entry port. The side-entry port facilitates return of retentate to the sump at a lower level in the vessel. Such feature has various benefits such as to facilitate flow of fluid into the smaller sump volume so that product is not retained within the larger disposable process bag (which could inhibit full recovery of the product). Alternatively or additionally, such feature encourages passive product mixing within the sump when the concentrated volume falls below the lower mixing impeller liquid interface. The sump may include one or more ridges, such as radially extending ridges, configured to prevent generation of strongly swirling flows/vortices generally associated with unbaffled stainless steel and single-use bioreactors. In some embodiments, the sump assembly is formed of a material considered by those of ordinary skill in the art to be disposable and accordingly may be considered to be a single-use component. Optionally, the sump may include an analytical instrument port, such as for measurement of pH, conductivity, etc.

In some embodiments, the disposable process bag includes a buffer spray ball as described above, such as a disposable spray ball. Because spray balls are typically used to clean reusable vessels, disposable process bag have not heretofore been provided with spray balls.

It will be appreciated that any or all aspects of components, system, and/or associated methods of use thereof in accordance with various principles of the present disclosure may be partially or fully automated. Various operational processes may be selected from a process menu via a human machine interface. Various pre-programmed processes may be monitored, controlled, and historically logged via software of a system formed in accordance with various principles of the present disclosure.

Various embodiments of a vessel, system incorporating such vessel, and methods of use thereof will now be described with reference to examples illustrated in the accompanying drawings. Reference in this specification to "one embodiment," "an embodiment," "some embodiments", "other embodiments", etc. indicates that one or more particular features, structures, and/or characteristics in accordance with principles of the present disclosure may be included in connection with the embodiment. However, such references do not necessarily mean that all embodiments include the particular features, structures, and/or characteristics, or that an embodiment includes all features, structures, and/or characteristics. Some embodiments may include one or more such features, structures, and/or characteristics, in various combinations thereof. Moreover, references to "one embodiment," "an embodiment," "some embodiments", "other embodiments", etc. in various places in the specification are not necessarily all referring to the same embodiment, nor are separate or alternative embodiments necessarily mutually exclusive of other embodiments. When particular features, structures, and/or characteristics are described in connection with one embodiment, it should be understood that such features, structures, and/or characteristics may also be used in connection with other embodiments whether or not explicitly described, unless clearly stated to the contrary. It should further be understood that such features, structures, and/or characteristics may be used or present singly or in various combinations with one another to create alternative embodiments which are considered part of the present disclosure, as it would be too cumbersome to describe all of the numerous possible combinations and subcombinations of features, structures, and/or characteristics. Moreover, various features, structures, and/or characteristics are described which may be exhibited by some embodiments and not by others. Similarly, various features, structures, and/or characteristics or requirements are described which may be features, structures, and/or characteristics or requirements for some embodiments but may not be features, structures, and/or characteristics or requirements for other embodiments. Therefore, the present disclosure is not limited to only the embodiments specifically described herein, and the examples of embodiments disclosed herein are not intended as limiting the broader aspects of the present disclosure.

It will be appreciated that common features in the drawings are identified by common reference elements and, for the sake of brevity and convenience, and without intent to limit, the descriptions of the common features are generally not repeated. For purposes of clarity, not all components having the same reference number are numbered. Moreover, a group of similar elements may be indicated by a number and letter, and reference may be made generally to one or such elements or such elements as a group by the number alone (without including the letters associated with each similar element). It will be appreciated that, in the following description, certain features in one figure may be used across different figures and are not necessarily individually labeled when appearing in different figures.

Figure 2:
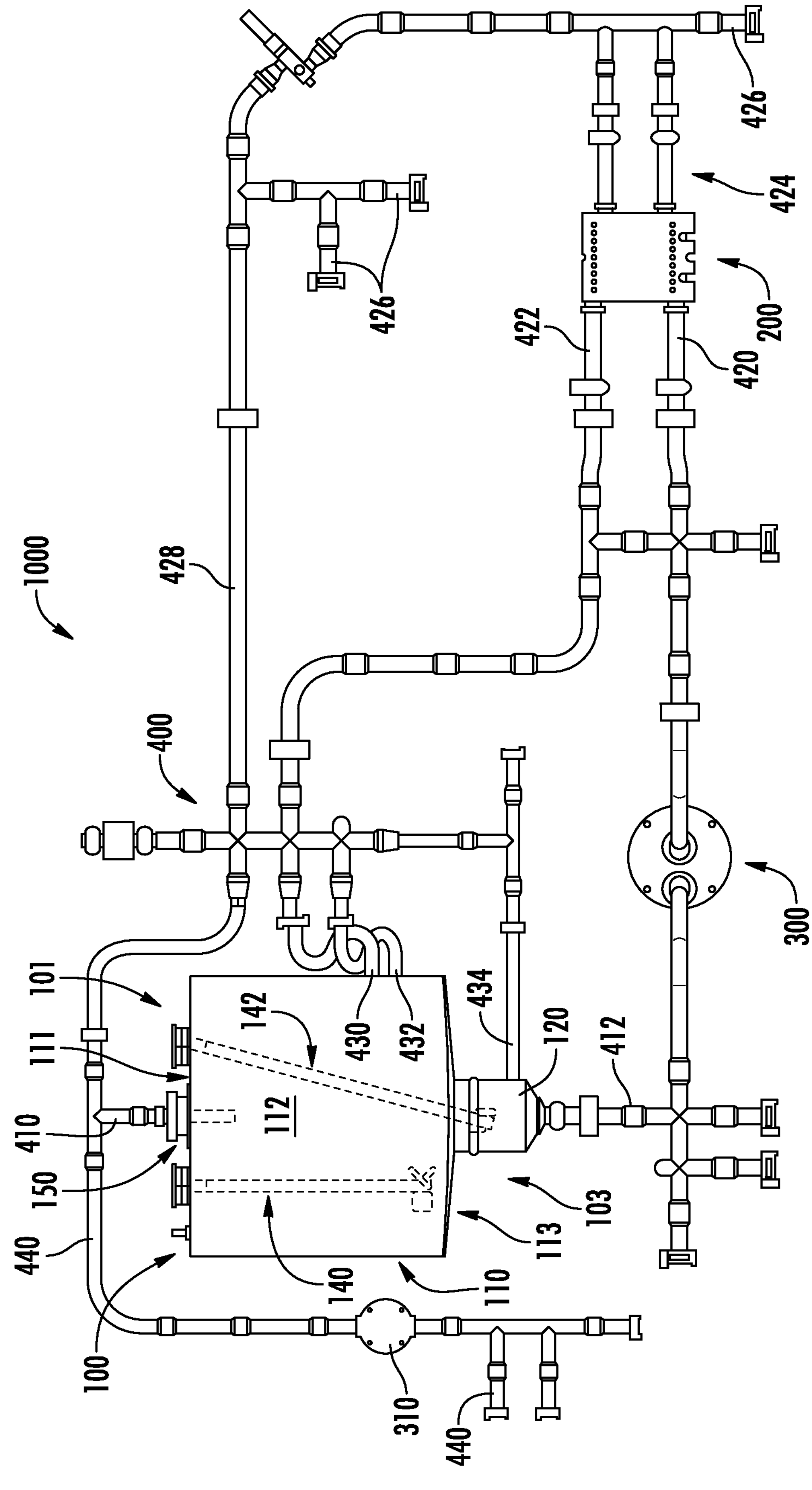
FIG. 2 illustrates an elevational view of a filtration system as in FIG. 1.

Turning now to the drawings, a fluid system 1000 (such as, without intent to limit, a bioprocessing and/or filtration system) in which a vessel 100 formed in accordance with various principles of the present disclosure may be used, is illustrated in FIG. 1 and FIG. 2. The fluid system 1000 may be configured for any of a variety of processes, including, but not limited to, filtration and volume reduction processes. For the sake of convenience, and without intent to limit, reference is made herein to filtration processes performed in filtration systems. However, it should be appreciated that the principles of the present disclosure are applicable to other processes as well as other fluid systems than those described herein.

As illustrated in FIG. 1 and FIG. 2, a non-limiting example of an embodiment of a fluid system 1000 includes a filter unit 200 and at least one pump 300, and a feed line assembly 400 forming flow paths between the vessel 100, the filter unit 200, the pump 300, and other devices, components, systems, etc., associated with the fluid system 1000. The filter unit 200 may be a tangential flow filtration ("TFF"), such as cassette filter or a filter with hollow fibers. In some embodiments, the filter unit 200 is an ultrafiltration unit. An additional pump 310 is illustrated as optionally being provided to pump materials (e.g., biological buffers, product introduction, etc.) into the fluid system 1000. The pumps 300, 310 may be any pump suitable for performing the desired operations of the fluid system 1000, including, without limitation, single-use four-diaphragm positive displacement recirculation pumps, peristaltic product/buffer pumps, peristaltic permeate pumps, etc.

It will be appreciated that not all feed lines of the feed line assembly 400 are independently indicated by a reference number. The various feed lines making up the feed line assembly 400 may be classified depending on their position within the various flow paths of the fluid system 1000, such as feedstream feed lines (e.g., for feeding biologic materials or feedstream into the fluid system 1000 for flowing through the fluid system 1000), buffer feed lines, filter feed lines (e.g., to feed feedstream into the filter unit 200), retentate lines (e.g., to feed retentate from the filter unit 200 back to the vessel 100), permeate lines (e.g., to remove permeate from the filter unit 200 out of the filter unit 200 and optionally out of the fluid system 1000 for collection or disposal), hydraulic lines, other ancillary lines, etc. The feed line assembly 400 may include pipes or tubing, including reusable tubing (e.g., sterilizable tubing, such as formed metal such as stainless steel) or disposable tubing (e.g., such as formed of polymers such as silicone), such tubing being optionally sterilizable. Polymeric tubing may be reinforced (e.g., braided silicone tubing), or unreinforced (e.g., silicone tubing, optionally platinum-cured, such tubing also being referenced as liners) and positioned within an exo-skeleton (e.g., metal outer tubing) which protects the unreinforced tubing from potential over-expansion (which may resulting in bursting of the tubing) or other undesired events. It will be appreciated that the present disclosure is not limited by the type of connector (e.g., tri-clamp, hose barb, etc.) used to couple a feed line of the feed line assembly 400 with another component or feed line. Preferably, the feed lines and/or tubing are designed to minimize hold-up volumes within the fluid system 1000.

Various additional components in the fluid system 1000 may include, without limitation, filters (e.g., tank vent filters such as used for a sterile air break between the outer atmosphere and the interior of the vessel, integrity test filters, air purge filters, etc.), flow meters (e.g., product flow meters, buffer flow meters, retentate flow meters, permeate flow meters, etc.), fluid containers (e.g., product containers, buffer containers, product collection containers, permeate collection containers, sample collection containers, etc.), valves (e.g., pinch valves, etc.), ports (e.g., outlet ports, inlet ports, etc.), sensors (e.g., conductivity sensors, temperature sensors, ultraviolet (UV) absorbance sensors, pH sensors, pressure sensors, compression load sensors, feed sensors, retentate sensors, permeate sensors, etc., including non-contact sensors), manifolds, etc.

In some embodiments, the fluid system 1000 is configured to filter a feed solution (hereinafter simply "solution" for the sake of convenience, and without intent to limit) therein to concentrate a selected product in the solution (e.g., proteins, cells, viruses, etc.). In such embodiment, the feed solution s fed through a system feed line 410 into the vessel 100. A pump 310 may be used to facilitating feeding of the solution and/or other materials (e.g., buffer) into the vessel 100. The solution is fed from the vessel 100 via a vessel outlet feed line 412 to the filter unit 200 via a filter inlet feed line 420. Retentate from the filter unit 200 is retained from the filter unit 200 via a retentate outlet feed line 422 and returned to the vessel 100. Permeate from the filter unit 200 is collected from the filter unit 200 via one or more permeate outlet feed lines 424. The permeate may be removed from the fluid system 1000 via one or more permeate outlet lines 426 (e.g., as a permeate drain flush, a permeate sample or waste collection, optional recirculation, etc.). In some embodiments, a buffer flush and air purge is performed, such as utilizing purging line 428.

In accordance with various principles of the present disclosure, a vessel 100 is configured to facilitate concentration of a product in the feedstream solution. For instance, the filter unit 200 may be configured to retain such product in the retentate stream flowing out of the filter unit 200. The filter unit 200 may be configured to remove fluid from the feedstream to reduce the volume of the feedstream to facilitate concentrating of the product of interest therein. In some embodiments, the product of interest is a protein, such as a virus or components thereof, and undesired materials (e.g., waste products, spent media from an upstream bioreactor process from which the feedstream was retrieved as permeate, etc.) are removed in the permeate flowing out of the filter unit 200.

Figure 3:
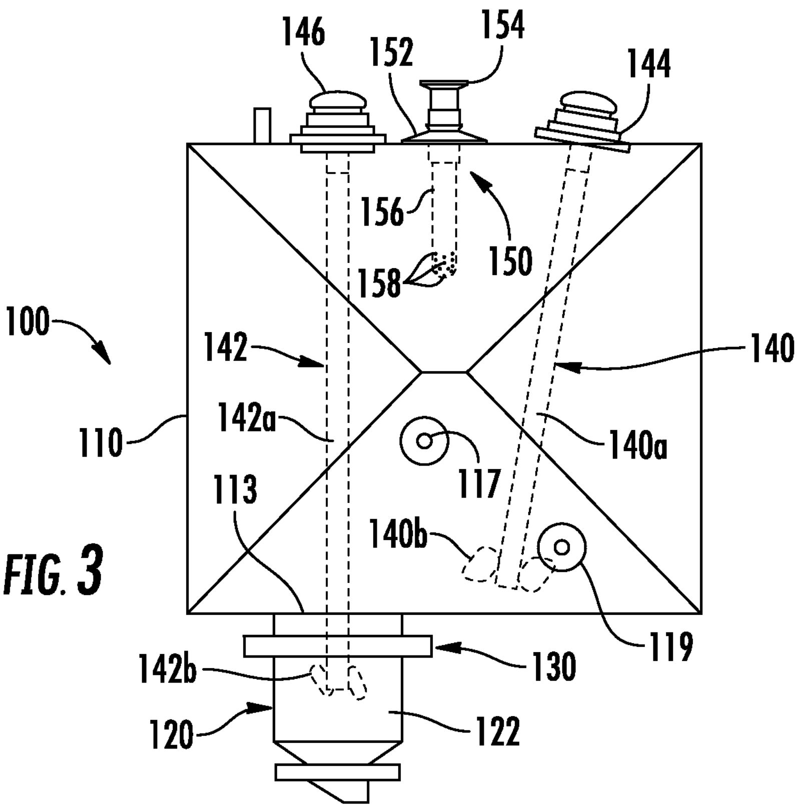
FIG. 3 illustrates a left side elevational view of an example of an embodiment of a containment vessel such as used in a filtration system as in FIG. 1 and FIG. 2.
Figure 4:
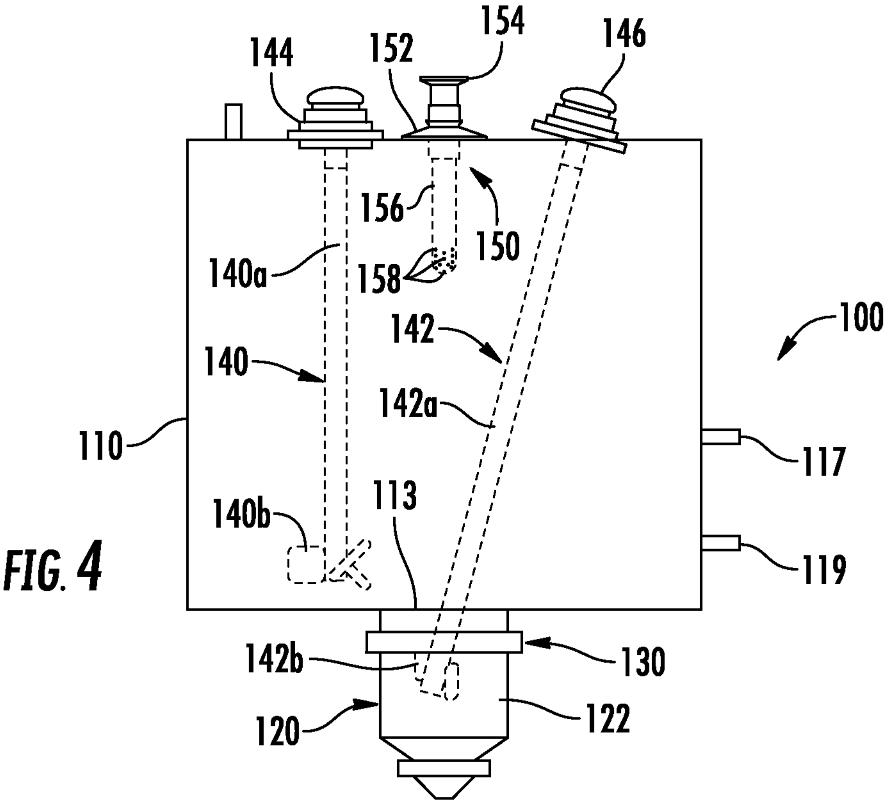
FIG. 4 illustrates a front elevational view of a containment vessel such as illustrated FIG. 3.

An example of an embodiment of a vessel 100 formed accordance with various principles of the present disclosure (and usable in the example of an embodiment of a fluid system 1000 as illustrated in FIG. 1 and FIG. 2) is illustrated independently in FIG. 3 and FIG. 4. In some embodiments, the vessel 100 is disposable, with various accompanying advantages and unique features as a disposable vessel 100 as described in further detail below. In some embodiments, of a disposable vessel 100, the vessel includes a main compartment or tank 110 formed of a material generally considered disposable in the industry in which the vessel 100 is to be used. For instance, the tank 110 may be in the form of a polymeric bag, such as formed of rigid, semi-rigid, or flexible polyethylene, polypropylene, or polysulfone. In some embodiments, the tank 110 fabricated from dual inner layers of ultra-low-density polyethylene (ULDPE), an ethylene vinyl alcohol polymer (EVOH) gas barrier layer, and an outer layer of polyethylene (PE). The tank 110 may be alternately referenced as a retentate bag without intent to limit. It will be appreciated that other materials and/or configurations of main compartments of a vessel 100 formed accordance with various principles of the present disclosure are within the scope and spirit of the present disclosure, the present disclosure not being limited in this aspect of the vessel 100. In some embodiments, a top entry sterile vent port 105 is provided.

In some embodiments, a vessel 100 is used, such as in a fluid system 1000, in connection with concentration of one or more products within the solution contained therein. Product concentration is generally accompanied by reduction in the overall volume of the solution containing the product. In some embodiments, very highly concentrated product is desirable, such as achieved by a one-hundred-fold reduction in volume of the initial solution. For instance, in some embodiments, the product may be concentrated from a starting volume (e.g, the volume of the solution fed into the vessel 100) of approximately 100-200 L to about 10 L, and, in some instances to about 6-8 L or less. Prior systems would require transfer of the solution to a different system for further concentration to the desired product concentration level. With the use of a sump assembly 120 formed in accordance with various principles of the present disclosure, the product may be further concentrated to result in a solution of less than about 2 L, and even about 1 L, within the sump vessel 122 thereof. An optimal level of concentration of product of interest in the solution may be achieved with a vessel 100 and sump assembly 120 formed in accordance with various principles of the present disclosure without the need for transferring the feedstream to another system for further processing as had been necessary in connection with prior art systems, as may be further appreciated in view of the following various aspects of the present disclosure.

To facilitate concentration of a product in a solution within a vessel 100 formed in accordance with various principles of the present disclosure, a sump assembly 120 is fluidly coupled to the tank 110 (such as at the bottom 113 of the tank 110 via a tank outlet port 115), as illustrated in FIG. 1 and FIG. 2, and in further detail in FIG. 3 and FIG. 4. In some embodiments, the sump assembly 120 is a single-use component, and may be formed of a material generally considered by those of ordinary skill in the art to be disposable (e.g., polysulfone), with various accompanying advantages as may be appreciated by those of ordinary skill in the art. The sump assembly 120 may be detachably coupled with the tank 110, such as with a connector 130. In some embodiments, the connector 130 is a clamp connector, such as a tri-clamp sanitary fitting.

Figure 5:
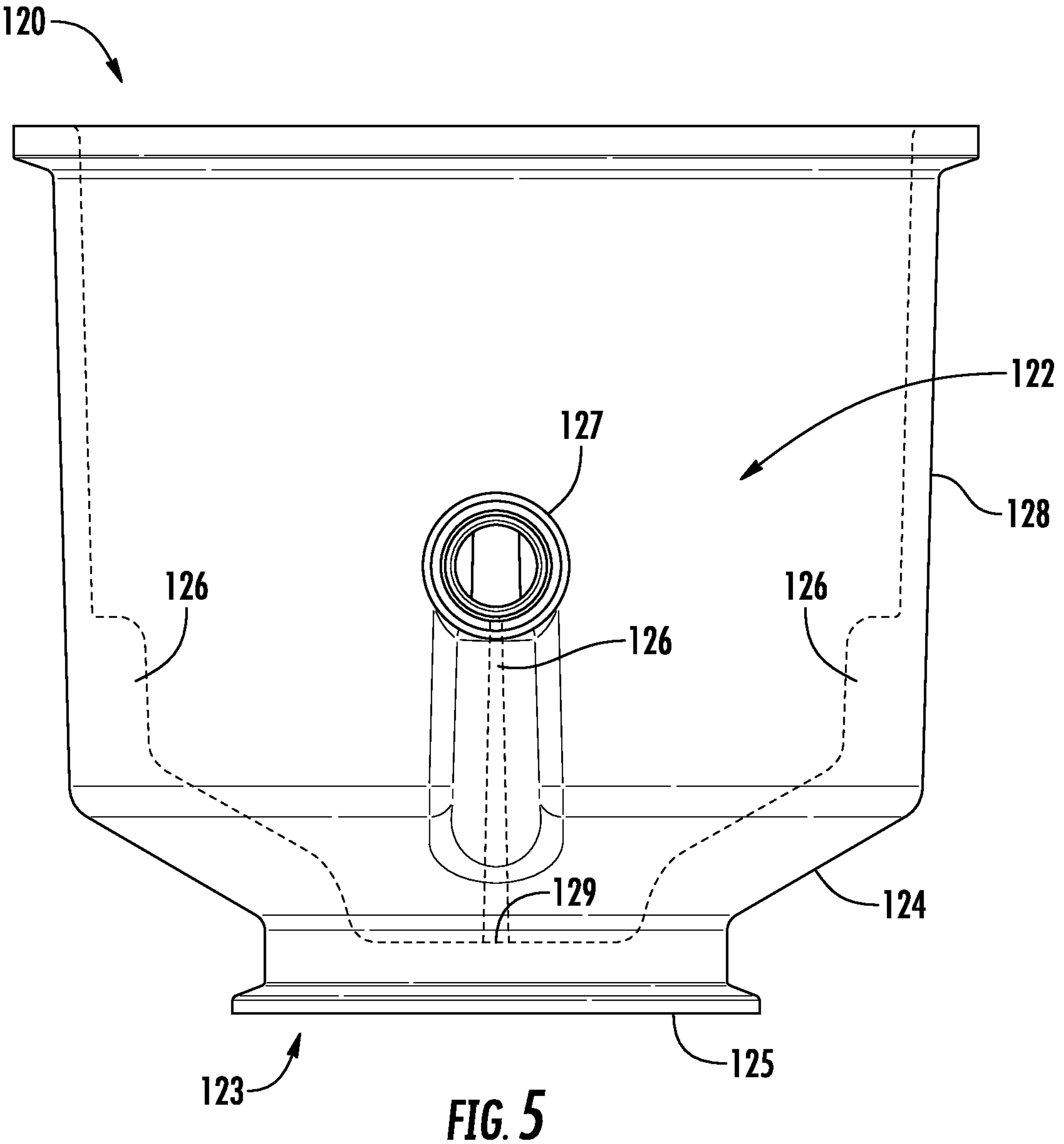
FIG. 5 illustrates a right side elevational view of an example of an embodiment of a sump which may be used with a containment vessel such as illustrated in FIG. 1, FIG. 2, FIG. 3, and/or FIG. 4.

The volume of the generally rigid sump vessel 122 of the sump assembly 120 is several orders of magnitude smaller than the volume of the tank 110. For instance, the tank 110 may contain at least about 100 L of fluid, such as a volume of approximately 150-200 L, whereas the sump vessel 122 may contain a volume of less than about 10 L of fluid, such as a volume of 3-5 L and even about 2 L of fluid. As will be appreciated, use of a reduced-volume sump vessel 122 provides various benefits over use of a larger vessel for concentrating a product in a feedstream. For instance, the reduction in cross-sectional area within the sump assembly 120 of the vessel 100 increases the height of the product within the vessel 100 and a side retentate return port 127 (discussed in further detail below) provides passive mixing, reducing the tendency of product to settle to the bottom of the vessel 100. Moreover, the reduction in cross-sectional area is accompanied by a reduction in the surface area of the bottom 103 of the vessel 100, which reduces the bottom surface of the vessel 100 along which product could collect (and to which product potentially may stick), thereby improving the ability to retrieve all of the potentially very expensive or otherwise valuable product from the fluid system 1000. In accordance with various principles of the present disclosure, as may be appreciated with reference to FIG. 5, showing an enlarged illustration of an example of an embodiment of a sump assembly 120, a generally conical funnel shaped section 124 may be provided between the sump vessel 122 and the bottom 123 of the sump assembly 120 to facilitate draining of the solution therein through the sump outlet port 125 to the vessel outlet feed line 412, for filtration through the filter unit 200 as discussed above.

In some embodiments, it is advantageous to provide a tank impeller 140 (which may alternately be referenced as a mixer, stirrer, etc.) to mix or agitate the feedstream, such as to maintain homogeneity/uniformity of the solution, to prevent settling of product within the feedstream, to prevent stratification of product along the interior of the walls 112 of the tank 110, and/or to prevent aggregation, agglomeration, coagulation, stratification, etc., of product (some components within the feedstream may tend to stick to one another, other components, and/or the interior of the tank 110), particularly when concentrating the product in the solution. For instance, as the product is concentrated in the feedstream and volume of the feedstream is reduced, the product may become increasingly, and even highly, viscous. The increase in product concentration (e.g., protein concentration) may be from a beginning value of about 50 mg/ml, and even as low as about 2.5 mg/ml, to a concentration of about 250-300 mg/ml, such as approaching the final desired product concentration. Use of a tank impeller 140 reduces such effects of concentration of the product in the solution, and may thereby facilitate movement of the feedstream through the fluid system 1000. The use of a tank impeller 140 also generally improves overall homogeneity of the solution.

It will be appreciated that as the volume of the feedstream within the fluid system 1000 in which the vessel 100 is used decreases, the level of feedstream within the tank 110 decreases as well. Such reduction in the feedstream level presents a challenge for the tank impeller 140 to adequately stir the solution within the tank 110. Advantageously, in accordance with various principles of the present disclosure, a sump impeller 142 is provided, extending into the sump assembly 120. As may be appreciated, use of a smaller sump vessel 122, such as provided by a sump assembly 120, formed in accordance with various principles of the present disclosure, may facilitate concentration of the product in the solution, as the smaller sump vessel 122 has a smaller diameter than the tank 110 to offset the reduced feedstream volume (and the consequent reduction in fluid height within the tank 110) Alternatively or additionally, the provision of a sump impeller 142 allows more effective stirring than may be achieved otherwise. It will be appreciated that once the level of the feedstream within the vessel 100 is below the tank 110 and contained within just the sump assembly 120, the tank impeller 140 may be switched off while the sump impeller 142 runs within the sump assembly 120.

In some embodiments, one or both impellers 140, 142 are formed of a single-use mixer shaft 140*a*, 142*a* and impeller assemblies 140*b*, 142*b* (including impeller blades), respectively, such as which may be advantageously used in connection with a single-use tank 110 and/or a single-use sump assembly 120. In some embodiments, one or both of the impellers 140, 142 are mounted with respect to the tank 110 via top-entry mixer connection flanges 144, 146, respectively. In some embodiments, at least one of the shafts 140*a*, 142*a* of the impellers 140, 142 is at an angle with respect to a vertical axis and/or at an angle with respect to the other shaft.

In some embodiments, the sump assembly 120 is positioned off-center from a midpoint of the bottom 113 of the tank 110, such as to allow sufficient room for both impellers 140, 142 to function optimally, and/or to facilitate user access thereto. In some embodiments, the impeller speeds are adjustable from 0 to approximately 300 RPM. It will be appreciated that any of a variety of drive assemblies may be used in connection with the impellers 140, 142 the details of which are not critical to the present disclosure.

In view of the above-described increase in concentration of product within the solution in the vessel 100, the viscosity of the product may increase. In accordance with various principles of the present disclosure ridges 126 may be provided extending inwardly within the sump vessel 122 from the sump vessel wall 128. The ridges 126 add strength to the wall 128 of the sump vessel 122, such as of a disposable sump assembly 120, particularly during molding. Alternatively or additionally, the ridges 126 may serve as mixing baffles, such as during passive retentate recirculation within the sump vessel 122. The ridges 126 may meet/cross outlet port 126 at the bottom 123 of the sump assembly 120 to form a vortex breaker 129 configured to disrupt potential vortices and/or to create a degree of turbulence sufficient to prevent undesired settling of product (which may occur because of the high concentration of product in the solution contained with the sump vessel 122). In some embodiments, three or four ridges 126 are provided. The ridges 126 may be equally spaced apart from one another or otherwise arranged to achieve the desired enhancement of fluid flow within the sump vessel 122, such as depending on one or more properties of the feedstream.

As described above, the reduction of volume of the feedstream as the product therein is concentrated by the fluid system 1000 reduces the feedstream level (i.e., height) within the vessel 100. In accordance with various principles of the present disclosure, feedstream (e.g., retentate from the filter unit 200) is returned to the vessel 100 at progressively lower levels with respect to the vessel 100. More particularly, as may be appreciated with reference to FIG. 2 and FIG. 3, instead of a retentate return line being fluidly coupled to the top 101 of the vessel 100 (such as in prior art vessels/systems), one or more retentate return lines 430, 432 are fluidly coupled to respective ports 117, 119 in a sidewall 112 of the tank 110 of the vessel 100. As such, the feedstream (e.g., in the form of retentate of a filter unit 200 within the fluid system 1000) may be returned at progressively lower levels as the total volume of feedstream in the fluid system 1000 is reduced. The number and location of the retentate return lines 430, 432 may be determined based on the volume level and diafiltration level in the system. Once the volume of the feedstream is below the level of the upper retentate return line 430, the feedstream is directed to the next lower retentate return line 432. Additional retentate return lines may be provided as appropriate for the fluid system 1000 and/or vessel 100 and/or feedstream therein. Advantageously, in accordance with various principles of the present disclosure, the retentate may ultimately be returned directly to the sump assembly 120 via a sump retentate return line 434 fluidly coupled with a port 127 in the wall 128 of the sump vessel 122.

It will be appreciated that provision, in accordance with various principles of the present disclosure, of feedstream return lines along the sidewalls of the vessel 100 (in contrast with through the top 101 of the vessel 100), and of more than one level of feedstream return line, allows the return lines to be kept below the feedstream level as the volume of the feedstream is reduced. As such, flow of the feedstream into the vessel 100 may remain submerged, thereby reducing potential splashing which may occur if the feedstream is returned above the level of the solution within the vessel 100. As may be appreciated, the higher the feedstream is returned above the level of solution within the vessel 100 the greater potential for splashing, and potential consequent adverse effects (e.g., foaming, which may be caused by interaction of products such as proteins with air, and which will denature and destroy a concentrated protein).

In some embodiments, it may be desirable to add buffer solution to the feedstream. For instance, a buffer solution may be added to perform a buffer exchange, such as in a diafiltration process, or for other purposes, such as to wash or otherwise treat materials (such as the product) within the feedstream solution. In accordance with various principles of the present disclosure, a spray ball 150, such as illustrated in FIG. 1, FIG. 2, FIG. 3, and FIG. 4, is provided to add materials into the feedstream in a gentler manner than in prior systems (which may cause splashing and/or foaming such as described above. The spray ball 150 may be configured to spray the buffer solution towards the sidewall 112 of the tank 110 rather than directly streaming the buffer solution onto the solution within the vessel 100 (such as commonly done in prior art systems). Such directional introduction of buffer solution may increase recovery of product from the fluid system 1000. The buffer solution sprayed along the interiors of the sidewall 112 of the tank 110 may help to remove product which may have stuck to the interiors of the sidewall 112 of the tank 110, thus maximizing recovery of product from the fluid system 1000.

In some embodiments, such as illustrated in FIG. 3 and FIG. 4, the spray ball 150 is mounted to the top 101 of the vessel 100, such as to the top 111 of the tank 110, via a mounting flange 152. A sanitary clamp 154, such as known in the art, may be provided to couple a buffer feed line 440 thereto, such as illustrated in FIG. 2. An O-ring (e.g., silicone) or other sealant may be used to assure fluid tight seals and to maintain sterility of the system. Buffer solution may be delivered through a hollow stem 156 of the spray ball 150 which extends from the mounting flange 152 into the interior of the vessel 100. The insertion length of the stem 156 may be determined by the height of the tank 110. For instance, the insertion length of the stem 156 designed to be at least approximately 3" (7.62 cm) above the maximum liquid level to be contained within the tank 110. Perforations 158 may be formed in the stem 156 in a spray pattern configured so that buffer solution is released laterally, towards the interior of the sidewall 112 of the tank 110. Such spray pattern adds the buffer solution in a gentler flow pattern which reduces potential splashing which may occur if the buffer solution were simply fed through a feed port as in prior art system, such as described above. Alternatively or additionally, such spray pattern facilitates the ability of the buffer solution to return to the solution any product which may have adhered to the interior of the sidewall 112 of the tank 110, such as described above. The number and angles of the perforations 158 through the stem 156 may be determined based on the fluid properties of the buffer solution and/or the flow rate and/or pressure at which the buffer solution is fed into the vessel 100 and/or the desired flow rate and projection distance of the buffer solution within the tank 110. It will be appreciated that reference to buffer solution is for the sake of convenience and materials in addition to or other than buffer solution may be added within the scope and spirit of the present disclosure.

In some embodiments, the spray ball 150 is formed of a material considered by those of ordinary skill in the art to be disposable, such as polypropylene. In some embodiments, the spray ball 150 is formed of a material which is sterilizable, such as by gamma or cobalt 60 irradiation. As such, components of the spray ball 150 may be sterilized, such as to kill potential spores thereon which would adversely affect the solution being processed and the product of interest. It will be appreciated that a disposable spray ball 150 may be used advantageously with a vessel 100 formed of disposable materials.

A vessel 100 as described above may be used advantageously in a filtration system, such as an ultrafiltration system. The vessel 100 may thus be considered a feed-retentate loop vessel. In use, the initial feed solution, with product therein to be concentrated, is fed, such as via an inlet feed line 440, such as illustrated in FIG. 1 and FIG. 2, into the vessel 100, such as through the top 101 of the vessel 100. The initial feed solution exits the vessel 100 via the bottom 103 of the vessel 100, such as via the outlet port 125 at the bottom 123 of the sump assembly 120, and is directed to the filter unit 200. The filter unit 200 may be an ultrafiltration unit configured to remove waste products in permeate, and to return proteins in retentate to the vessel 100 for further concentration to a final concentration level of product to be used in a further process. Buffer solution may be added via a spray ball 150 as described above to further enhance the filtration and product concentration process. Various ports (illustrated but not individually labeled in FIG. 1 and FIG. 2) for accessing the feedstream within fluid system 1000 and/or the tank 110 of the vessel 100, may be provided, such as for instrumentation purposes (e.g., a pH probe or other sensors for analytical measurements of properties of the feedstream and/or components thereof). The fluid system 1000 may perform multiple filtration cycles, volume changes, and/or washes to achieve a desired concentration of target product in the feedstream.

Figure 6:
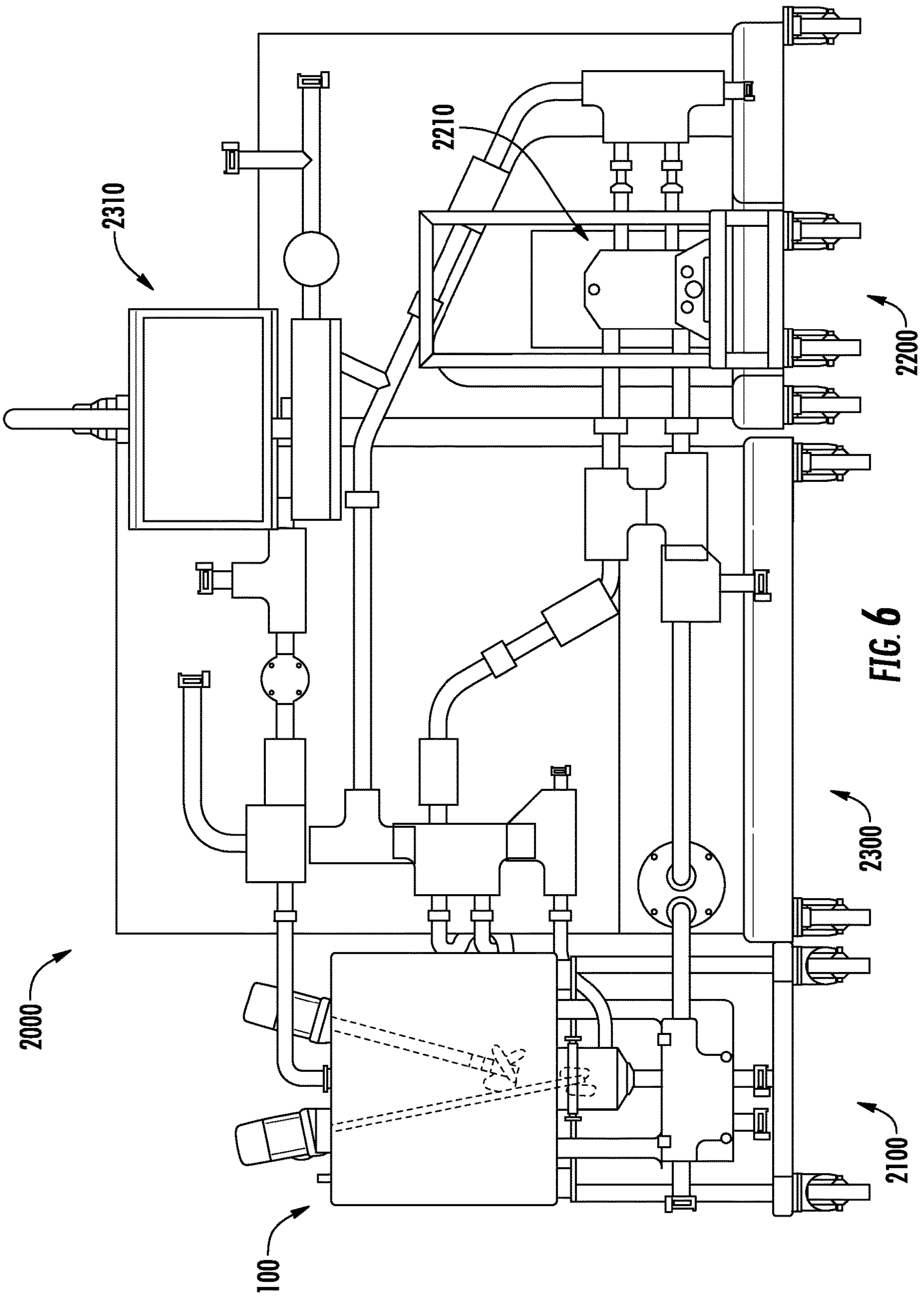
FIG. 6 illustrates an elevational view of a modular filtration system in which a filtration system as in FIG. 1 and FIG. 2 may be used.

A TFF system using a vessel 100 formed in accordance with various principles of the present disclosure may be configured as a modular system 2000, such as illustrated in FIG. 6. As illustrated, a vessel 100 formed in accordance with various principles of the present disclosure may be provided on a vessel cart 2100, and the filter unit 200 may be provided on a separate filtration cart 2200, optionally detachable from the vessel cart 2100. In some embodiments, a TFF holder 2210 is provided on the filtration cart 2200 and is configured to accommodate multiple filter units 200 in the form of filter cassettes so that the cassette assembly may be removed as a unit and moved to a separate location for chemical cleaning. In some embodiments, the feed line assembly 400 fluidly coupling the vessel 100 with the filter unit 200 may be provided on a separate fluid flow cart 2300, which optionally may also carry various control units for controlling, monitoring, regulating, etc., the fluid system 1000. A user interface 2310 (such as a computer, or a monitor, or information display) may be provided on the fluid flow cart 2300 to facilitate monitoring and/or operation of the fluid system 1000. It will be appreciated that each of the carts 2100, 2200, 2300 may be separable from the other, and may be readily movable for adjustment, storage, independent operation (such as at another location). etc.

It will be appreciated that vessels, fluid systems, and methods in accordance with various principles of the present disclosure allow for rapid concentration (in a shorter time than previously achieved) of products in a given solution, to optimal set points, and with minimal product loss (e.g., by maximizing the ability to recover product from the system, and/or by reducing potential agglomeration or aggregation or other adverse effects on the product of interest which may be caused by prior systems or methods) in a single system. In some embodiments, a fluid system 1000 formed in accordance with various principles of the present disclosure, such as with a vessel 100 formed in accordance with various principles of the present disclosure, may be used to process a batch of material clarified from a bioreactor, downstream of the bioreactor, such as a protein rich batch of material. Vessels, systems, and methods in accordance with various principles of the present disclosure may be particularly advantageous for use in concentrating cells, monoclonal antibodies, lentiviruses, adenoviruses, etc.

Various features, aspects, or the like of a vessel or process system may be used independently of, or in combination, with each other. It will be appreciated that a vessel and/or system as disclosed herein may be embodied in many different forms and should not be construed as being limited to the illustrated embodiments of the figures, such as described herein. Rather, these embodiments are provided so that this disclosure will convey certain aspects of a vessel and/or process system formed in accordance with various principles of the present disclosure to those skilled in the art.

It should be understood that, as described herein, an "embodiment" (such as illustrated in the accompanying Figures) may refer to an illustrative representation of an environment or article or component in which a disclosed concept or feature may be provided or embodied, or to the representation of a manner in which just the concept or feature may be provided or embodied. However such illustrated embodiments are to be understood as examples (unless otherwise stated), and other manners of embodying the described concepts or features, such as may be understood by one of ordinary skill in the art upon learning the concepts or features from the present disclosure, are within the scope of the disclosure. In addition, it will be appreciated that while the Figures may show one or more embodiments of concepts or features together in a single embodiment of an environment, article, or component incorporating such concepts or features, such concepts or features are to be understood (unless otherwise specified) as independent of and separate from one another and are shown together for the sake of convenience and without intent to limit to being present or used together. For instance, features illustrated or described as part of one embodiment can be used separately, or with one or more other features to yield a still further embodiment. Thus, it is intended that the present subject matter covers such modifications and variations as come within the scope of the appended claims and their equivalents.

In view of the above, it should be understood that the various embodiments illustrated in the figures have several separate and independent features, which each, at least alone, has unique benefits which are desirable for, yet not critical to, the presently disclosed vessel, system, and associated method. Therefore, the various separate features described herein need not all be present in order to achieve at least some of the desired characteristics and/or benefits described herein. Only one of the various features may be present in a vessel or system formed in accordance with various principles of the present disclosure. Alternatively, one or more of the features described with reference to one embodiment can be combined with one or more of the features of any of the other embodiments provided herein. That is, any of the features described herein can be mixed and matched to create hybrid designs, and such hybrid designs are within the scope of the present disclosure. Moreover, throughout the present disclosure, reference numbers are used to indicate a generic element or feature of the disclosed embodiment. The same reference number may be used to indicate elements or features that are not identical in form, shape, structure, etc., yet which provide similar functions or benefits. Additional reference characters (such as letters, as opposed to numbers) may be used to differentiate similar elements or features from one another.

The foregoing discussion has broad application and has been presented for purposes of illustration and description and is not intended to limit the disclosure to the form or forms disclosed herein. It will be understood that various additions, modifications, and substitutions may be made to embodiments disclosed herein without departing from the concept, spirit, and scope of the present disclosure. In particular, it will be clear to those skilled i the art that principles of the present disclosure may be embodied in other forms, structures, arrangements, proportions, and with other elements, materials, and components, without departing from the concept, spirit, or scope, or characteristics thereof. For example, various features of the disclosure are grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations. While the disclosure is presented in terms of embodiments, it should be appreciated that the various separate features of the present subject matter need not all be present in order to achieve at least some of the desired characteristics and/or benefits of the present subject matter or such individual features. One skilled in the art will appreciate that the disclosure may be used with many modifications or modifications of structure, arrangement, proportions, materials, components, and otherwise, used in the practice of the disclosure, which are particularly adapted to specific environments and operative requirements without departing from the principles or spirit or scope of the present disclosure. For example, elements shown as integrally formed may be constructed of multiple parts or elements shown as multiple parts may be integrally formed, the operation of elements may be reversed or otherwise varied, the size or dimensions of the elements may be varied. Similarly, while operations or actions or procedures are described in a particular order, this should not be understood as requiring such particular order, or that all operations or actions or procedures are to be performed, to achieve desirable results. Additionally, other implementations are within the scope of the following claims. In some cases, the actions recited in the claims can be performed in a different order and still achieve desirable results. The presently disclosed embodiments are therefore to be considered in all respects as illustrative and not restrictive, the scope of the claimed subject matter being indicated by the appended claims, and not limited to the foregoing description or particular embodiments or arrangements described or illustrated herein. In view of the foregoing, individual features of any embodiment may be used and can be claimed separately or in combination with features of that embodiment or any other embodiment, the scope of the subject matter being indicated by the appended claims, and not limited to the foregoing description.

In the foregoing description and the following claims, the following will be appreciated. The phrases "at least one", "one or more", and "and/or", as used herein, are open-ended expressions that are both conjunctive and disjunctive in operation. The terms "a", "an", "the", "first", "second", etc., do not preclude a plurality. For example, the term "a" or "an" entity, as used herein, refers to one or more of that entity. As such, the terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, counterclockwise, and/or the like) are only used for identification purposes to aid the reader's understanding of the present disclosure, and/or serve to distinguish regions of the associated elements from one another, and do not limit the associated element, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another.

The following claims are hereby incorporated into this Detailed Description by this reference, with each claim standing on its own as a separate embodiment of the present disclosure. In the claims, the term "comprises/comprising" does not exclude the presence of other elements, components, features, regions, integers, steps, operations, etc. Additionally, although individual features may be included in different claims, these may possibly advantageously be combined, and the inclusion in different claims does not imply that a combination of features is not feasible and/or advantageous. In addition, singular references do not exclude a plurality. Reference signs in the claims are provided merely as a clarifying example and shall not be construed as limiting the scope of the claims in any way.

What is claimed is:

1. A fluid vessel for use in a bioprocessing system, the fluid vessel comprising:

a vessel tank having a top, a sidewall, and a plurality of inlet ports defined in the sidewall;

a sump assembly having an open upper end fluidly coupled below said vessel tank, the sump assembly having a sidewall with an inlet port defined therein, said sump assembly having a sump vessel with an internal volume for holding fluid smaller than an internal volume of said vessel tank; and a first impeller having first impeller blades disposed in the vessel tank configured to stir fluid within said vessel tank, the first impeller including a first mixer shaft mounted to the vessel tank via a first mixer-connection flange, and a separately controllable second impeller having second impeller blades disposed in the sump assembly configured to stir fluid in said sump vessel, the second impeller including a second mixer shaft mounted to the vessel tank via a second mixer-connection flange;

wherein at least one of the first and second mixer shafts is oriented at an oblique angle with respect to a vertical axis of the vessel tank; and wherein the first and second mixer-connection flanges are mounted to the top of the vessel tank.

2. The fluid vessel of claim 1, wherein the plurality of inlet ports comprises a first inlet port and a second inlet port, said second inlet port being lower than said first inlet port to deliver feedstream into said vessel tank at a lower height than delivered through said first inlet port.

3. The fluid vessel of claim 1, wherein said vessel tank is formed of a disposable polymeric material.

4. The fluid vessel of claim 1, wherein said sump assembly is formed of a disposable material.

5. The fluid vessel of claim 1, wherein at least one ridge extends inwardly from a sidewall of said sump vessel.

6. The fluid vessel of claim 5, wherein said at least one ridge forms a vortex.

7. The fluid vessel of claim 1, wherein said vessel tank is configured to contain at least 100 L of fluid, and said sump vessel is configured to contain no more than about 10 L of fluid.

8. The fluid vessel of claim 1, further comprising a spray ball extending from the top of said fluid vessel into said vessel tank and formed of a disposable material.

9. The fluid vessel of claim 8, wherein said spray ball is configured to spray buffer solution into said vessel tank directed to the interior of the sidewall of said vessel tank.

10. A single-use fluid vessel for use in a bioprocessing system, the single-use fluid vessel comprising:

a vessel tank formed of a disposable material, the vessel tank having a top, a sidewall, and plurality of inlet ports defined in the sidewall;

a spray ball, formed of a disposable material, extending from the top of said fluid vessel into said vessel tank;

a sump assembly having an open upper end fluidly coupled below said vessel tank and having an inlet port defined in a side wall thereof; and a first impeller having first impeller blades disposed in the vessel tank configured to stir fluid within said vessel tank, the first impeller including a first mixer shaft mounted to the vessel tank via a first mixer-connection flange, and a separately controllable second impeller having second impeller blades disposed in the sump assembly configured to stir fluid in said sump vessel, the second impeller including a second mixer shaft mounted to the vessel tank via a second mixer-connection flange;

wherein at least one of the first and second mixer shafts is oriented at an oblique angle with respect to a vertical axis of the vessel tank; and wherein the first and second mixer-connection flanges are mounted to the top of the vessel tank.

11. The fluid vessel of claim 10, wherein said spray ball is formed of an irradiatable sterilizable material.

12. The fluid vessel of claim 10, wherein said spray ball includes a hollow stem having a plurality of perforations therethrough configured to direct material through said hollow stem towards the interior of the sidewall of said vessel tank.

13. The fluid vessel of claim 10, wherein said spray ball is configured to spray buffer solution into said vessel tank directed to the interior of the sidewall of said vessel tank to return materials stuck on the interior of the sidewall of said vessel tank to fluid contained within said vessel tank.

14. The fluid vessel of claim 10, wherein said vessel tank is formed of a flexible polymeric material.

15. A bioprocessing system for processing a fluid solution, said system comprising:

a fluid vessel comprising a vessel tank having a top, a sidewall, and a first volume, and a sump assembly having a second volume smaller than the first volume, the sump assembly having an open upper end and a sidewall, the open upper end fluidly coupled to a bottom of said vessel tank;

a first impeller having first impeller blades disposed in the vessel tank configured to stir fluid within said vessel tank, the first impeller including a first mixer shaft mounted to the vessel tank via a first mixer-connection flange, and a separately controllable second impeller having second impeller blades disposed in the sump assembly configured to stir fluid in said sump vessel, the second impeller including a second mixer shaft mounted to the vessel tank via a second mixer-connection flange;

wherein at least one of the first and second mixer shafts is oriented at an oblique angle with respect to a vertical axis of the vessel tank; and wherein the first and second mixer-connection flanges are mounted to the top of the vessel tank;

a processing system; and a fluid line assembly fluidly coupling said vessel tank and said sump assembly with said processing system, and comprising:

a vessel outlet feed line fluidly coupling said fluid vessel with said processing system;

a first return line fluidly coupled with the sidewall of said vessel tank at a first height along said fluid vessel to return fluid processed in said processing system to said vessel tank;

a second return line fluidly coupled with the sidewall of said vessel tank at a second height along said fluid vessel lower than the first height to return fluid processed in said processing system to said vessel tank; and a sump return line fluidly coupled with the sidewall of said sump assembly below said first return line and said second return line.

16. The system of claim 15, wherein said processing system comprises a filter unit.

17. The system of claim 15, wherein said system further comprises a spray ball configured to spray material through the top of said vessel tank and towards an interior of the vessel tank sidewall.

18. The system of claim 17, wherein said spray ball is coupled to a feed line for buffer solution and is configured to spray buffer solution towards the interior of the vessel tank sidewall.

19. The system of claim 17, wherein said spray ball is formed of a disposable irradiatable material.

20. The system of claim 15, wherein at least one of said vessel tank and at least a portion of said sump vessel is formed of a disposable material.

* * * * *